(12) United States Patent
Cartwright et al.

(10) Patent No.: US 9,057,111 B2
(45) Date of Patent: Jun. 16, 2015

(54) DIAGNOSTIC METHODS AND MARKERS FOR BACTERIAL VAGINOSIS

(71) Applicant: Laboratory Corporation of America Holdings, Burlington, NC (US)

(72) Inventors: Charles Paul Cartwright, Plymouth, MN (US); Bryndon Denae Lembke, Eden Prairie, MN (US); Kalpana Ramachandran, Shakopee, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 90 days.

(21) Appl. No.: 13/771,550

(22) Filed: Feb. 20, 2013

(65) Prior Publication Data

US 2013/0288988 A1 Oct. 31, 2013

Related U.S. Application Data

(60) Provisional application No. 61/600,845, filed on Feb. 20, 2012.

(51) Int. Cl.
*C12Q 1/68* (2006.01)
(52) U.S. Cl.
CPC ............ *C12Q 1/689* (2013.01); *C12Q 2600/16* (2013.01)
(58) Field of Classification Search
CPC ............................ C12Q 1/689; C12Q 2600/16
USPC ............................................ 435/6.12; 514/24
See application file for complete search history.

(56) References Cited

U.S. PATENT DOCUMENTS

| 7,625,704 | B2 | 12/2009 | Fredricks et al. |
| 7,745,595 | B2 | 6/2010 | Trama et al. |
| 2010/0075306 | A1† | 3/2010 | Bretelle |
| 2010/0226899 | A1† | 9/2010 | Osborn |
| 2011/0053802 | A1† | 3/2011 | Forney |
| 2012/0264126 | A1† | 10/2012 | Johnson |
| 2013/0316922 | A1† | 11/2013 | Balashov |

OTHER PUBLICATIONS

American College of Obstetricians and Gynecologiest, Vaginitis, ACOG Practice Bulletin No. 72, Obstet Gynecol, 107:1195-1206 (2006).
Amsel, R., et al., "Nonspecific Vaginitis," Am. J. Med., 74:14-22, (1983).
Biagi, E. et al., "Quantitative variations in the vaginal bacterial population associated with asymptomatic infections: a real-time polymerase chain reaction study," Eur. J. Clin. Microbiol. Infect. Dis., 28:281-285, (2008).
Brotman, R.M. et al., "Ready or Not: The Molecular Diagnosis of Bacterial Vaginosis," Clin. Infect. Dis., 47:44-46, 2008.
Cartwright, C.P. et al., "Development and Validation of a Semiquantitative, Multitarget PCR Assay for Diagnosis of Bacterial Vaginosis," Journal of Clinical Microbiology, 50(7):2321-2329, (2012).
Cauci, S. et al., "Prevalence of Bacterial Vaginosis and Vaginal Flora Changes in Peri- and Postmenopausal Women," J. Clin. Microbiol., 40:2147-2152, (2002).
Dumonceaux, T.J., et al., "Multiplex Detection of Bacteria Associated with Normal Microbiota and with Bacterial Vaginosis in Vaginal Swabs by Use of Oligonucleotide-Coupled Fluorescent Microspheres," J. Clin. Microbiol., 47(12):4067-4077, (2009).
Eckert, L.O., "Acute Vulvovaginitis," N. Engl. J. Med., 355:1244-1252, (2006).
Ferris, M.J., et al., "Association of *Atopobium vaginae*, a recently described metronidazole resistant anaerobe, with bacterial vaginosis," BMC Infect. Dis., 4:1-8, (2004).
Ferris, M.J., et al., "Cultivation-Independent Analysis of Changes in Bacterial Vaginosis Flora Following Metronidazole Treatment," J. Clin. Microbiol., 45(3):1016-1018, (2007).
Fredricks, D.N., et al., "Molecular Identification of Bacteria Associated with Bacterial Vaginosis," N. Engl. J. Med., 353:1899-1911, (2005).
Fredricks, D.N., et al., "Targeted PCR for Detection of Vaginal Bacteria Associated with Bacterial Vaginosis," J. Clin. Microbiol., 45(10):3270-3276, (2007).
Fredricks, D.N., et al., "Changes in Vaginal Bacterial Concentrations with Intravaginal Metronidazole Therapy for Bacterial Vaginosis as Assessed by Quantitative PCR," J. Clin. Microbiol, 47(3):721-726, (2009).
Hale, L.P., et al., "Bacteria Associated with Bacterial Vaginosis [correspondence]," N. Engl. J. Med, 354(2):202-203, (2006).
Hay, P.E., "National Guideline for the Management of Bacterial Vaginosis," Royal Society of Medicine, London, United Kingdom, http://www.bashh.org/documents/62/62.pdf. (2006).
Hillier, S.L., "The Complexity of Microbial Diversity in Bacterial Vaginosis," N. Engl. J. Med., 353(18):1886-1887, (2005).
Ison, C.A., et al., "Validation of a simplified grading of Gram stained vaginal smears for use in genitourinary medicine clinics," Sex Transm. Infect., 78:413-415, (2002).
LABupdate, "Bacterial Vaginosis by NAA," Laboratory Corporation of America Holdings, (Oct. 2011).
Leitich, H., et al., "Bacterial vaginosis as a risk factor for preterm delivery: A meta-analysis," Am. J. Obstet. Gynecol., 189:139-147, (2003).
Menard, J-P., et al., "Molecular Quantification of *Gardnerella vaginalis* and *Atopobium vaginae* Loads to Predict Bacterial Vaginosis," Clin. Infect. Dis., 47:33-43, (2008).
Nugent, R.P., et al., "Reliability of Diagnosing Bacterial Vaginosis is Improved by a Standardized Method of Gram Stain Interpretation," J. Clin. Microbiol, 29(2):297-301, (1991).
Ravel, J., et al., "Vaginal microbiome of reproductive-age women," Proc. Natl. Acad. Sci. U.S.A., 1-8, (2011).

(Continued)

*Primary Examiner* — Brandon Fetterolf
*Assistant Examiner* — Yin-Horng Shiao
(74) *Attorney, Agent, or Firm* — Kilpatrick Townsend & Stockton LLP

(57) ABSTRACT

A method of diagnosing bacterial vaginosis in a woman, which involves determining an amount of each of more than one BV-associated bacterium in a vaginal sample obtained from the female and assessing a BV status of the female based on the amount of each of the more than one BV-associated bacterium in the sample.

11 Claims, 2 Drawing Sheets

(56) References Cited

OTHER PUBLICATIONS

Sha, B.E., et al., "Utility of Amsel Criteria, Nugent Score, and Quantitative PCR for *Gardnerella vaginalis, Mycoplasma hominis*, and *Lactobacillus* spp. for Diagnosis of Bacterial Vaginosis in Human Immunodeficiency Virus-Infected Women," J. Clin. Microbiol., 43(9):4607-4612, (2005).

Sherrill, C.B., et al., "Nucleic Acid Analysis Using an Expanded Genetic Alphabet to Quench Fluorescence," J. Am. Chem. Soc., 126:4550-4556, (2004).

Spiegel, C.A. "Bacterial Vaginosis," Clin. Microbiol. Rev., 4(4):485-502 (1991).

Tamraker, R., et al., "Association between *Lactobacillus* species and bacterial vaginosis-related bacteria, and bacterial vaginosis scores in pregnant Japanese women," BMC Infec. Dis., 7(128):1-8, (2007).

U.S. Preventative Services Task Force, Screening for Bacterial Vaginosis in Pregnancy to Prevent Preterm Delivery: US Preventative Services Task Force Recommendation Statement, Ann. Intern. Med., 148:214-219, (2008).

Wiesenfeld, H.C., et al., "Bacterial Vaginosis is a Strong Predictor of *Neisseria gonorrhoeae* and *Chlamydia trachomatis* Infection," Clin. Infect. Dis., 36:663-668, (2003).

Zozaya-Hinchliffe, M., et al., "Quantitative PCR Assessments of Bacterial Species in Women with and without Bacterial Vaginosis," J. Clin. Microbiol., 48(5):1812-1819, (2010).

Verhelst et al., "Cloning of 16S rRNA genes amplified from normal and disturbed vaginal microflora suggests a strong association between *Atopobium vaginae, Gardnerella vaginalis* and bactaerial vaginosis," 2004, BioMed Central, 4:1-11.†

Verstraelen et al., "Culture-independent analysis of vaginal microflora: The unrecognized association of *Atopobium vaginae* with bacterial vaginosis," 2004, Elsevier, 191:1120-2.†

Trama et al., "Rapid detection of *Atopobium vaginae* and association with organisms imlicated in bacterial vaginosis," 2007, Elsevier Ltd., 22(2):96-102.†

Oakley et al., "Diversity of Human Vaginal Bacterial Communities and Associations with Clinically Defined Bacterial Vaginosis," 2008, American Society for Microbiology, 74(15):4898.†

Hummelen et al., "Deep Sequencing of the Vaginal Microbiota of Women with HIV," 2010, PLoS ONE, 5(8):e12078.†

† cited by third party

Figure 1. Distribution of qPCR values on development phase samples by Nugent Category for markers used in final BV PCR construct; *Atopobium vaginae* (A), BVAB-2 (B), *Megasphaera*-1 (C). Positions of cut-off calibrators, Cal-1 (a) and Cal-2 (b) are shown.

Total Score: 5

Interpretation: Positive

DIAGNOSTIC METHODS AND MARKERS FOR BACTERIAL VAGINOSIS

RELATED APPLICATIONS

This application claims the benefit of priority of U.S. Provisional Application Ser. No. 61/600,845, filed Feb. 20, 2012, and incorporated herein by reference in its entirety.

FIELD

The methods described herein are in the general field of clinical testing, including the field of diagnosing and monitoring of diseases and conditions.

BACKGROUND

One of the common conditions experienced by women throughout their lives is vaginitis, which is typically characterized in the medical field as an inflammation of the vagina that can result in discharge, itching and pain. There are several potential etiologies of vaginitis, including candidal vaginitis, typically caused by overgrowth with the commensal fungal organism *Candida albicans*, trichomonal vaginitis, which is a sexually transmitted infection (STI) caused by a protozoan parasite *Trichomonas vaginalis*, vaginal atrophy, or atrophic vaginitis, which results from reduced estrogen levels during menopause, and bacterial vaginosis or vaginitis, which is associated with a perturbation in the in the composition of the bacterial microflora of the vagina. Vaginitis symptoms may include change in color, odor or amount of discharge from a woman's vagina, vaginal itching or irritation, pain during intercourse, painful urination, and light vaginal bleeding or spotting. Vaginitis symptoms can lead to various degrees of physical and emotional discomfort, and lower the overall quality of life. Vaginitis symptoms can also be a sign of an underlying infection, which should be promptly identified and treated in order to avoid medical complications, and, in case of an STI, to avoid further transmission.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Covered by the patent embodiments of the invention are defined by the claims, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

Provided herein are improved methods useful for diagnosing bacterial vaginosis which can be also referred to in this patents as BV diagnostic methods, tests or assays, or other similar terms. BV diagnostic methods of the present invention are probative for vaginal microflora alterations underlying BV, and use objective quantitative measures of bacterial occurrence in vaginal samples. The improved BV diagnostic methods are accurate, cost-effective, clinically predictive and readily interpretable. Generally, the improved BV diagnostic methods described herein use appropriate analytical procedures to detect and quantify molecular markers from several categories of bacteria in a vaginal sample. For example, the improved BV diagnostic methods of the present invention can use quantitative or semi-quantitative assays for detection of bacterial DNA sequences, such as quantitative PCR, semi-quantitative PCR or direct nucleic acid detection assays, in order to quantitatively or semi-quantitatively detect DNA sequences characteristic of several bacterial categories in a vaginal sample. The categories of bacteria quantitatively detected by the improved methods can be bacterial species or genera.

Categories of bacteria, also referred to as bacterial markers, are selected for detection by the BV diagnostic methods of the present invention in such a way as to provide a clinically meaningful assessment, based on the results of detection, of the likelihood of BV in a woman from whom the vaginal sample was obtained. The improved BV diagnostic methods interrogate vaginal samples for the presence of more than one bacterial marker, and derive a combined result from those markers that directly correlates with the presence or absence of BV. The bacterial markers are selected for the improved BV diagnostic methods of the present invention based on their probative value, when the markers are used collectively, for this assessment of BV status of a vaginal sample. Some embodiments of the BV diagnostic methods described herein advantageously employ at least one marker that has high specificity with respect to BV detection in a patient population, and at least one marker that has high sensitivity with respect to BV detection in a patient population. The selection of the bacterial markers used in the improved BV diagnostic methods can vary and can be based on a number of factors, such as the health risks associated with particular markers or certain patient characteristics, such as pregnancy or HIV status, as well as BV prevalence in a patient population. The methods and procedures for selecting the bacterial markers to be used in the BV diagnostic methods are included within the scope of the present invention, as well as the combinations of bacterial markers described herein used for diagnosing, predicting or assessing BV in a patient.

The improved BV diagnostic methods of the present invention characterize the bacterial markers detected in a sample using a scoring method, which is then translated into a clinical interpretation of a BV status of the sample. The scoring method used in the improved BV diagnostic methods assigns scores to individual bacterial markers and generates a composite score when more than one bacterial marker is used. The scoring method uses the data on distribution of the levels of BV marker organisms in a patient population in order to divide the population into the categories characterized by scores reflecting the levels of the marker in each category. The scoring method used in the improved BV diagnostic methods is included within the scope of the present invention.

Among other things, described herein is a method of diagnosing bacterial vaginosis in a female, comprising: determining an amount of more than one BV-associated bacterium in a sample obtained from the female; and, assessing a BV status of the female based on the amount of each of the more than one BV-associated bacterium in the sample. In one embodiment of the method, the more than one BV-associated bacterium is three bacteria. In one more embodiment of the method, more than one BV-associated bacterium includes *Atopobium vaginae*, BVAB-2, and *Megasphaera*-1. In another embodiment of the method, the more than one BV-associated bacterium also includes *Gardnerella vaginalis*. In an alternative embodiment, more than one BV-associated bacterium does not include *Gardnerella vaginalis*. In yet another embodiment, the more than one BV-associated bacterium does not include a *Lactobacillus* bacterium. In an alternative embodiment, the more than one BV-associated bacterium includes a *Lactobacillus* bacterium. In a variation of the above embodiments, the *Lactobacillus* bacterium is *Lactobacillus crispatus*.

One embodiment of the diagnostic methods described herein is a method of diagnosing bacterial vaginosis in a female, comprising: determining an amount of at least *Atopobium vaginae*, BVAB-2 or *Megasphaera*-1 in a sample obtained from the female; and, assessing a BV status of the female based on the amount of each of the more than one BV-associated bacterium in the sample, wherein an increased amount of one or more of *Atopobium vaginae*, BVAB-2 or *Megasphaera*-1 indicates an increased probability of the female having BV. An amount of the *Lactobacillus* bacterium in the sample can also be determined, wherein an increased amount of the *Lactobacillus* bacterium indicates a decreased probability of the female having bacterial vaginosis.

In some of the diagnostic methods according to the present invention, the step of determining comprises detection of DNA sequences from the each of the more than one BV-associated bacterium. The detection of DNA sequences can be performed by quantitative PCR, semi-quantitative PCR or direct DNA probe detection. Methods of detecting bacterial vaginosis in pregnant females are included within the scope of the present invention.

The methods of the present invention provide reproducible and objective ways of evaluating vaginal microflora in women with signs and symptoms of vaginitis, and are at least comparable in diagnostic accuracy to the conventional gold standard for diagnosis of BV. The methods of the present invention employ simple and robust scoring systems and methods that allow for accurate differentiation of BV positive and negative samples to be performed in a standardized and cost-effective manner. An exemplary embodiment of a method of diagnosing bacterial vaginosis in a female, comprises: determining an amount of each of more than one BV-associated bacterium in a sample obtained from the female; assigning a score to the sample based on the amount of each of the more than one BV-associated bacterium detected in the sample, and, assessing the BV status of the female based on the score assigned to the sample. The step of assigning the score can comprise generating an individual score for each of the more than one BV-associated bacterium detected in the sample based on the amount of the each of the more than one BV-associated bacterium; and, calculating the combined score from the individual scores.

DETAILED DESCRIPTION

Figure 1:
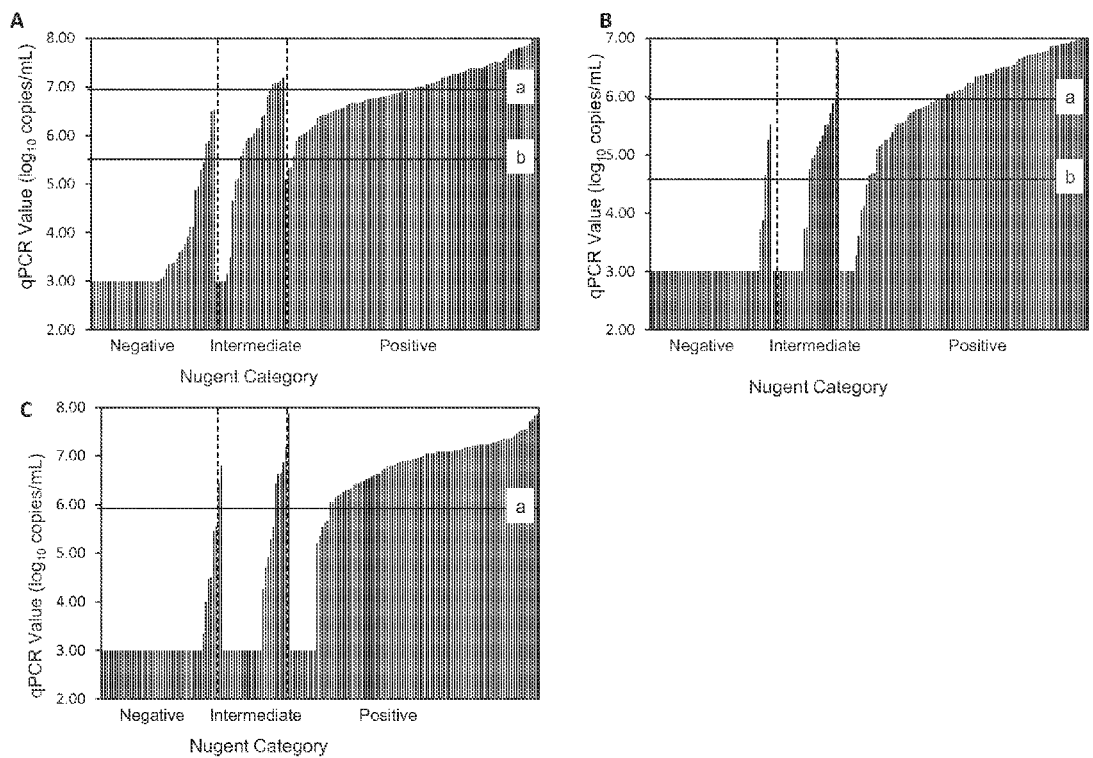
FIG. 1 is a bar graph illustrating frequency distribution of *Atopobium vaginae* (panel A), BVAB-2 (panel B) and *Megasphaera*-1 (panel C) in the each of the three Nugent categories of the samples of the first sample group (as discussed in the working examples). Vertical axis shows organism concentration as determined by qPCR. Positions of cut-off calibrators or values, denoted as Cal-1 (a) and Cal-2(b), with respect to the organism concentrations are shown by horizontal lines.

Treatment for vaginitis is determined based on its causes and origins in a particular patient. For example, fungal vaginitis should be treated by an antifungal medication, applied topically or taken in an oral form, while trichomoniasis is treated by a different type of antibiotic medication (typically oral metronidazole or tinidazole). Estrogen, in the form of vaginal creams, tablets or rings, is often prescribed to treat atrophic vaginitis, while BV may be treated by anti-bacterial medications, including the antibiotics metronidazole and clindamycin. Some forms of vaginitis are a result of irritation of vaginal lining by common consumer products, such as soaps or lubricants, or particular types of undergarment, and the treatment may be as simple as stopping the use of an irritating product.

Since vaginitis has a variety of underlying causes, it is important to identify the cause in order to determine correct treatment. An inappropriate choice of treatment may not only delay the relief of the vaginitis symptoms in a woman, but also lead to medical complications and spread of an infection to the woman's sexual partners. Choosing an inappropriate drug for vaginitis (for example, an antifungal medication for BV, metronidazole for fungal infection, or an antibiotic for a fungal infection) may lead to unnecessary side effects and cause drug resistance. Delayed diagnosis and inappropriate choice of treatment can also result in emotional and financial losses for the woman, elevated treatment costs, and generally contribute to increases in healthcare spending and inefficiencies in healthcare delivery.

Whilst the presence of specific symptoms can sometimes be instructive in determining an etiology, misdiagnosis is common. Diagnostic procedures by a qualified practitioner are typically required to detect whether an infection is present, and to determine the nature of the infection. Diagnostic procedures often include microscopy, usually of a vaginal wet mount sample, and culture of the vaginal discharge. The color, consistency, acidity, and other characteristics of the discharge may be predictive of the causative agent. However, definitive identification of infectious organisms is very important for the successful treatment, because women may have more than one infection, or have symptoms that overlap with those of another infection.

Bacterial vaginosis (BV), one of the possible causes of vaginitis, is a condition marked by an imbalance in vaginal flora. Although the precise etiology and pathophysiology of BV is not fully understood, this syndrome accounts, by some estimates, for about 22 to 50% of vaginitis symptoms. BV has been linked to a variety of serious health risks for the woman herself and others. For example, BV has been linked to increased chances of preterm labor and delivery, which increases the chances of the woman's baby dying or having serious medical problems. BV was also linked to pelvic inflammatory diseases (PID), a condition in which bacteria infect the uterus and/or fallopian tubes. PID can cause infertility or damage the fallopian tubes, thus increasing the chances of ectopic pregnancy, a life-threatening condition. Some studies showed that pregnant women with BV are more likely to contract infections following genital surgery, such as hysterectomy or an abortion. BV has also been linked to increased susceptibility to HIV infection after exposure to HIV virus, increased risk of transmission of HIV, as well as an increased susceptibility to other STIs, such as herpes simplex virus (HSV), *Chlamydia trachomatis*, and *Neisseria gonorrhoeae*.

While many questions remain about the role of different bacterial species in BV causation, current BV theories explain the condition as replacement of the normal, homogeneous, vaginal microflora (dominated typically by hydrogen-peroxide producing *lactobacilli*) with a heterogeneous mix of anaerobic and microaerophilic organisms. Diagnosis of BV has thus been defined by techniques that attempt to either identify this shift in bacterial composition, or assess the concomitant impact of this shift on non-microbiological indicators of vaginal health, or a combination of both of these approaches.

The standards against which diagnostic tests for BV are compared include the so-called Amsel criteria and the Nugent Gram-stain scoring system. BV diagnosis under the Amsel criteria requires that at least three of four of the following criteria are met for a given patient: characteristic vaginal discharge; vaginal pH>4.5; positive amine test, meaning release of a primary amine (fishy) odor from a vaginal sample on the addition of the KOH, and >20% of the epithelial cells present on the wet mount slide of the vaginal discharge being identified as 'clue cells' (meaning they are coated with small Gram-variable coccobacilli consistent with the organism *Gardnerella vaginalis*). While still widely touted as a useful diagnostic approach, the Amsel criteria are not commonly used in routine practice, and since this method requires innately subjective evaluations of samples, wide fluctuations in accuracy have been reported. Under optimal circumstances, Amsel-based diagnosis of BV is generally regarded in the medical field as a relatively specific but somewhat insensitive method for identifying patients with BV.

The Nugent Gram-stain scoring system, which was more recently developed than the Amsel criteria, involves assessment of a normally prepared Gram stain for relative abundance of three morphotypes of bacteria, and then calculating the so-called Nugent score based on the amounts of large Gram-positive rods (*Lactobacilli* morphotype; decrease in *Lactobacilli* is scored as 0 to 4), small Gram-negative and variable rods (*Bacteroides* and *Gardnerella* morphotype; scored as 0 to 4), and curved gram-variable rods (*Mobiluncus* spp. morphotype; scored as 0 to 2). The Nugent score can range from 0 to 10, with scores of 0-3 deemed normal (non-BV), 4-6 intermediate, and 7-10 positive for BV. The Nugent scoring system is somewhat more objective than the Amsel criteria, and is regarded as a more reproducible and predictive means of diagnosing BV. However, Nugent scoring still requires preparation and evaluation of slides, and is dependent on the skill of the slide reader. In addition to being generally subjective, since many of the key morphotypes are difficult to differentiate from non-contributory organisms of similar appearance, quantitative Gram-stain examination is laborious and impractical for routine clinical use, and intermediate scores of uncertain clinical significance are reported in 10-25% of samples tested.

Cultures of vaginal samples have not proven useful for diagnosing BV. Since a hallmark of the condition is a complex perturbation of the normal vaginal microflora, culture-based identification of single 'marker' organisms lacks both sensitivity and specificity. Many putative BV-associated organisms, such as *Gardnerella vaginalis, Mobiluncus* spp., *Mycoplasma hominis*, or *Bacteroides* spp., can comprise variable fractions of the vaginal microflora in women without BV, compromising the specificity of culture-based testing. In addition, many of the key organisms associated with BV are obligate anaerobes and either difficult to recover or unrecoverable using conventional culture methods, which makes a true evaluation of vaginal microflora by culture impossible.

A more current diagnostic approach is the use of tests designed to detect BV-related organisms, directly or indirectly. One so-called "indirect" approach is the BV Blue® test (Gryphus diagnostics, LLC). The BV Blue test detects sialidase activity, an enzyme produced by BV-associated bacteria such as *Gardnerella vaginalis, Bacteroides* spp., *Prevotella* spp., and *Mobiluncus* spp. In the test procedure, a vaginal fluid sample is placed in the test vessel which contains a chromogenic substrate for sialidase. After incubation, a developer solution is added, and If the sample contained a high level of sialidase, a blue or green color is seen. Samples containing no sialidase, or low levels of this enzyme, will generate a yellow color in the reaction. The BV test is claimed to have high specificity and sensitivity, but has a number of limitations. For example, specimens from the BV Blue test have to be collected from the lower one-third of the vaginal wall, because cervical sialidase activity may give a false positive test result. Various vaginal products, such as creams, ointments, spermicides or vaginal lubricants, used by patients, may interfere with the enzymatic reaction. In addition, samples have to either tested immediately upon collection, or stored and transported under specific conditions to prevent loss of enzymatic activity.

The Affirm® Microbial Identification Test (Beckton Dickinson) ("Affirm test") is an example of a direct specimen DNA probe-based diagnostic test for the differential detection and identification of the three types of vaginitis causative organisms: *Candida* spp., *G. vaginalis* and *T. vaginalis*. The Affirm test is convenient for a clinician, since it offers the results for three different organisms from a single sample. For BV diagnosis, the test relies on the detection of elevated concentrations of *G. vaginalis*. While the Affirm test offers the ability to improve the accuracy and objectivity of vaginitis diagnosis, and is not as prone to external interferences as the BV Blue test, it is also known to be less specific than the Nugent Gram-stain scoring approach.

One unresolved issue with the Affirm assay is that it relies on the notion that *G. vaginalis* functions as a uniquely predictive marker for BV, a concept known not to be accurate in the medical field. A more nuanced (and commonly accepted) view of BV in the field is that the hallmark of this condition is an increase in the diversity of the vaginal microbiome, with the composition of the BV-associated flora being highly complex, and lacking a single 'signature' organism Whilst elevated levels of *G. vaginalis* such as those detected by the Affirm assay are frequently found in women with BV syndrome, they also occur in a subset of women without this condition, and without the ability to simultaneously assess the presence of other potential BV marker organisms, the specificity of the Affirm assay is compromised.

The use of a variety of DNA-based analysis tools, such as broad-range and quantitative PCR, has identified novel bacteria associated with BV while also providing more objective, quantitative measures of bacterial presence. Use of DNA-based tools also has resulted in a greater awareness of the complexity of microflora alterations underlying BV. A number of studies have been published describing the use of quantitative or semi-quantitative PCR methodologies for diagnosing BV. The marker organisms used in these studies differed, as did the cut-off values described as optimal for differentiating abnormal samples from normal samples. There is, as yet, no unified approach to using PCR technology for BV diagnosis.

In summary, currently available BV diagnostic methods suffer from various disadvantages. The currently accepted diagnostic standards, namely the Amsel criteria and the Nugent Gram-stain score, rely heavily on the proficiency of the individual clinician and/or laboratory, and are effectively impossible to standardize. Simple indirect laboratory tests such as the BV Blue test, are prone to problems in sensitivity (loss of enzyme activity) and specificity (inappropriate sample collection) and are thus of limited value. The Affirm test relies on direct detection of bacterial DNA and improved accessibility and is easier to employ than the known approaches discussed above, but allows for only qualitative detection of a single organism (*G. vaginalis*), and thus lacks diagnostic accuracy.

What is needed is an improved diagnostic method for detecting BV in patients. Such an improved method would be accurate, cost-effective to perform, clinically predictive and readily interpretable, while simultaneously being compatible with tests for alternate etiologies of vaginitis (eg *Candida* spp. and *T. vaginalis*) and other STIs (such as chlamydia and gonorrhea). The improved BV diagnostic method would take into account more than one BV-associated organism, and at the same time would be readily interpretable by a clinician, who would be able either to use the data from the improved test to diagnose BV in a patient, or combine, according to an established and easy to perform procedure, the results from the improved tests with other available diagnostic methods in order to achieve diagnosis of BV in a patient with high level of accuracy.

Provided herein are improved methods useful for diagnosing bacterial vaginosis (BV). Generally, the methods for diagnosing BV described herein involve determining an amount or concentration of more than one BV-associated bacteria, or marker, in a vaginal sample, and determining the BV status of the patient from the amount of the BV-associated bacteria present in the sample. Unlike some of the conventional methods that rely on the observation of a vaginal sample (in the form or a microscope slide) by a trained person, such as a clinician, the methods of the present invention use objective, quantifiable measures of bacterial occurrence in samples, namely, the presence of specific bacterial molecules, which are referred to as molecular markers. Such markers are detected according to established and reliable techniques and procedures. Accordingly, the methods of the present invention are less dependent on the subjective acumen of the person performing the method than methods involving microscopic examination.

The term "bacterial vaginosis," abbreviated as "BV," and similar terms used herein are to be understood in the broad sense as the alterations of vaginal bacterial flora composition in a woman, as compared to a baseline, reference or "normal" vaginal bacterial flora composition. In other words, the term "bacterial vaginosis" and related terms are not limited to a specific vaginal bacterial flora composition or any particular symptoms observed in a particular woman or population of women. While BV can manifest itself through a variety of symptoms, some of which are discussed elsewhere in this document, BV can also be asymptomatic. In certain situations, BV may be considered a medical condition or disease that requires treatment, while in other situations BV may be viewed as a benign variation of the vaginal bacterial flora. Regardless of the specific definition of BV, or the baseline or reference bacterial flora used, BV diagnostic methods described herein are generally probative for vaginal microflora alterations, and can be used to determine such alterations in both symptomatic and asymptomatic females.

Improved methods useful for diagnosing BV can be also referred to as BV diagnostic methods, tests or assays. All these terms can be used interchangeably and fall within the scope of the present invention. "Diagnosis," "diagnosing," and related terms refer generally to a process or result of BV detection, identification or determination. The terms diagnosis, detection, identification, determination, assaying, testing and related terms, when used in reference to BV or in the context of the methods of the present invention can denote showing, indicating, discovering or determining one or more of presence of BV, absence of BV, prevalence, progression, level or severity of BV, as well as a probability of BV, present or future occurrence or exacerbation of symptoms of BV, consequences or complications of BV, or to efficacy of a treatments. The foregoing list is not intended to be exhaustive, and these terms "diagnose," "detect," "indicate," "identify," "indicative," "determine," "assay," "test" and similar terms can also refer to other things.

The molecular markers detected in the methods of the present invention are exemplified by bacterial nucleic acids, such as DNA or RNA. The nucleic acid markers are nucleic acid sequences specific to a particular category of BV-associated bacteria, such as a bacterial species or a genus. For example, the molecular markers used in some embodiments of the present invention are nucleic acid sequences specific to one or more the following bacteria: *Atopobium vaginae*, Bacterial Vaginosis Associated Bacterium (such as BVAB-1, BVAB-2 or BVAB-3), *Megasphaera*-1, *G. vaginalis*, or *Lactobacillus crispatus*. However, the molecular markers of the present invention are not limited to the nucleic acid sequences of the above-listed bacterial species. It is understood that other currently known bacteria can be used as BV markers in the embodiments of the present invention, and that newly recognized bacteria can be cultured from the samples or detected in libraries of clones from subjects with BV and used as markers in the embodiments of the present invention. It is envisioned that the methods of the present invention can be modified to detect a variety of BV-associated bacteria, and the molecular markers used in a particular embodiment of the methods of the present invention would be modified accordingly.

The detection of nucleic acids employed in some embodiments of the methods described in this patent is less prone to environmental interferences and user errors, as compared to the so-called "indirect" assays of metabolic or enzymatic activity. Also, the nucleic acid markers employed in some of the embodiments of the methods of the present invention allow for specific detection of various bacterial species, unlike the non-specific enzymatic or metabolite markers that can be produced by several different bacteria. The nucleic acid markers used in the embodiments of the methods described herein, as well as the probes for detection of the markers, can be selected or modified to allow for more or less specific detection of various bacterial groups. For example, some of the markers or the probes can be selected to detect whole genera of bacteria, such as *Lactobacillus*, while the other embodiments may employ markers or probes that detect specific bacterial species. Various markers and probes can be selected and modified in order to choose a combination of markers and probes with an optimal predictive value desired for a particular situation. Thus, the methods of the present invention allow for increased assay flexibility in the test design, and can be easily adapted for a particular patient subgroup, purpose, or to account for new information on bacterial populations.

BV diagnostic methods according to the present invention and its various embodiments use quantitative measures of bacterial occurrence in vaginal samples. The term "occurrence," when used in reference to the bacteria detected according to the embodiments of the present invention is used to denote incidence of the bacteria, as well as frequency of their appearance, quantity, or distribution throughout different categories and subcategories. Combination of such information on the occurrence of bacteria can be referred to as a "pattern." The information on occurrence of bacteria, or bacterial patterns, obtained from the samples investigated in the course of performing the BV diagnostic methods according to the present invention, can be compared or correlated with the information on bacterial occurrence in other samples, or to the information obtained by other methods from the same samples. Such information can be obtained prior to, concurrently with, or subsequently to the performance methods of the present invention. It is to be understood that any information used for comparison can be processed and stored, including processing and storage in computer form. Occurrence of bacteria is used in some embodiments of the present invention as a characteristic measured and evaluated as an indicator of BV. Some other embodiments of the present invention use the information on the occurrence of bacteria to identify the categories or combinations of bacteria that can be used as markers of BV in a patient.

Detection of BV according to various embodiments of the methods disclosed herein can employ appropriate analytical methods, techniques or procedures. In some embodiments of the detection methods, quantitative or semi-quantitative PCR is employed to detect bacterial markers. However, it is envisioned that other suitable analytical techniques can be employed in other embodiments, such as immunochemical techniques or mass-spectroscopy. In one embodiment, a multiplexed quantitative PCR assay is used to detect several molecular markers in a sample simultaneously. The categories of bacteria quantitatively detected by the improved methods can be bacterial species or genera.

The term "sample," as used in this patent, refers to any sample suitable for testing or assaying according to the methods of the present invention. One example of a sample can be referred to as a gynecological sample, such as a vaginal swab obtained according to the procedures accepted in the medical field. However, the term "sample" is not limited to vaginal swabs, but can also be used to describe discharge or mucus samples, tissue sample or cell samples, obtained, processed, transported and stored using various suitable procedures. For examples, the samples can be stored in suitable storage or transportation devices, refrigerated, frozen, desiccated, diluted, mixed with various additives, or mounted on slides.

The BV-associated bacteria detected using the molecular markers described herein are also referred to as "bacterial markers" and belong to a variety of bacterial genera and species. Some of the genera are *Lactobacillus, Atopobium, Gardnerella, Mobiluncus, Bacteroides, Leptotrichia, Sneathia, Porphyromonas*, and *Mycoplasma*. Some of the bacterial species are *Atopobium vaginae*, BVAB-2, *Megasphaera*-1, *Lactobacillus crispatus*, and *Gardnerella vaginalis*. The terms "bacterial marker" or "bacterial markers" are used herein to refer to one or more bacteria, or certain combinations of bacteria, whose occurrence can be used for assessment of BV status of a vaginal sample. Bacterial markers are selected for detection by the BV diagnostic methods of the present invention so as to provide a clinically meaningful assessment, based on the results of detection, of the occurrence of BV in a woman from whom the vaginal sample was obtained. The amount or presence of a bacterial marker in a sample can be positively or negatively correlated with the presence of BV in a patient from whom the sample was obtained. Accordingly, the marker can be referred to as a negative or a positive marker.

Some of the bacterial markers utilized by the present invention are normal inhabitants of a human body, and are often referred to as "commensal" bacteria, particularly when they are not associated with any pathological states or conditions. Some other bacteria can be described as "pathological," particularly if they are typically not found in human body, or found in low numbers, and their presence or increased numbers is associated with a pathological state. It is noted that the same bacterial species can be classified as both "commensal" or "pathological," depending on the accepted classification system, pathology paradigm, bacterial numbers, and other factors. The present invention is therefore not limited to the using commensal, pathological, or any other category of bacterial markers.

The bacterial markers are selected for the embodiments of the present invention in order to provide improved diagnostic characteristics with respect to determination of the BV status of a female patient. The selection of the bacterial markers can be modified or adjusted to improve or optimize diagnostic characteristics of the BV diagnostic methods of the present invention in a patient population. Such diagnostic characteristics can be also referred to as "probative value." Some criteria for assessment of probative value are predictive value, sensitivity, and specificity. The term "predictive value" is used herein to denote a parameter that is used to characterize a correlation between the presence of BV in a patient or a group of patient and the occurrence of a particular bacterium or groups of bacteria. "Predictive value" can reflect positive correlation and be referred to as "positive predictive value," or can reflect negative correlation and be referred to as "negative predictive value." The terms "sensitivity" and "specificity" are used herein to refer to statistical measures of the performance of diagnostics tests. Sensitivity refers to a proportion of positive results which are correctly identified by a test. Specificity measures a proportion of the negative results that are correctly identified by a test. Examples of the calculations used to determine predictive value (positive and negative), specificity and specificity are described elsewhere in this patent.

Diagnostic methods or tests according to some embodiments of the present invention advantageously use at least one bacterial marker that has high specificity, and at least one bacterial marker that has high sensitivity. It was discovered that employing a combination of at least two markers with these characteristics achieves improved probative value for a BV diagnostic test. The term "high specificity" refers to specificity that is equal or over 80%, 81%, 82%, 83%, 84%, 85%, 86%, 87%, 88%, 89%, 90%, 91%, 92%, 93%, 94%, 95%, 96%, 97%, 98%, or 99%. In one example, high specificity refers to specificity of approximately over 90%. In another example, high specificity refers to specificity of approximately over 95%. The term "high sensitivity" refers to sensitivity that is equal or over 80%, 81%, 82%, 83%, 84%, 85%, 86%, 87%, 88%, 89%, 90%, 91%, 92%, 93%, 94%, 95%, 96%, 97%, 98%, or 99%. In one example, high sensitivity refers to sensitivity of approximately over 90%. In another example, high sensitivity refers to sensitivity of approximately over 95%. The selection of the bacterial markers used in the improved BV diagnostic methods of the present invention can depend on a number of factors, such as the patient characteristics or the health risks associated with particular markers or patient characteristics. The diagnostic tests according to some embodiments of the present invention can advantageously use at least one bacterial marker that has high specificity but low sensitivity, and at least one bacterial marker that has high sensitivity but low specificity. The term "low sensitivity" refers to sensitivity that is equal or less than 75%, 76%, 77%, 78%, 79%, 80%, 81%, 82%, 83%, 84%, 85%, 86%, 87%, 88%, 89%, 90%, 91%, 92%, 93%, 94% or 95%. In one example, low sensitivity refers to specificity of approximately less than 78%. In another example, low sensitivity refers to sensitivity of approximately less than 89%. The term "low specificity" refers to specificity that is equal or less than 75%, 76%, 77%, 78%, 79%, 80%, 81%, 82%, 83%, 84%, 85%, 86%, 87%, 88%, 89%, 90%, 91%, 92%, 93%, 94% or 95%. In one example, low specificity refers to specificity of approximately less than 78%. In another example, low specificity refers to specificity of approximately less than 89%. The positive predictive value for the BV diagnostic methods according to the embodiments of the present invention can range from approximately 50% to approximately 99%. For example, positive predictive value can be approximately 55%, 58%, 76%, 85% or 90%. Negative predictive value for the BV diagnostic methods according to the embodiments of the present invention can range from approximately 95% to approximately 99.5%. For example, negative predictive value can be approximately 98%, 98.5%, 99% or 99.5%. The methods according to embodiments of the present invention can have increased positive predictive value, as compared to previously known tests. For example, positive predictive value can be approximately 20-40%, 22-33% higher, or 25-30% higher than the positive predictive value for a conventional test in a given population.

Markers selected for BV diagnosis may be different for different patient populations. For example, different bacterial markers may be selected for populations with different prevalence of BV. In other examples, different bacterial markers may be selected for different ethnic or age groups, or have different baseline or reference vaginal bacterial populations. The selection of bacterial markers may be changed based on the distribution of various markers in a particular patient population in both a baseline (non-BV) state and BV states of various severities. In another example, different bacterial markers may be selected for detecting BV in pregnant women than for non-pregnant women. In one more example, different bacterial markers may be used to detect BV in HIV-positive and HIV negative patients, depending on the health risks associated with different bacteria for each of the groups.

In one embodiment of the BV diagnostic method described in this patent, a combination of *A. vaginae*, BVAB-2, *G. vaginalis*, *Megasphaera*-1 and *L. crispatus* is used to delineate BV. In another embodiment, a combination of *A. vaginae*, BVAB-2, *G. vaginalis*, *Megasphaera*-1 is used as a marker for BV. In another embodiment, *L. crispatus* is included in a group of bacterial markers as a negative predictor for BV. The number of bacterial markers used in various embodiments of the present invention can be two, three, four, five, six, seven, eight or higher. The methods and procedures for selecting the bacterial markers to be used in the BV diagnostic methods are included within the scope of the present invention, as well as the combinations of bacterial markers described herein, which are used for diagnosing, predicting or assessing BV in a patient.

The improved BV diagnostic methods characterize the bacterial markers detected in a sample using a scoring method, which is then translated into a clinical interpretation of a BV status of the sample. The scoring method used in the improved BV diagnostic methods assigns scores to individual bacterial markers based on their levels, determined as amount or concentration of a bacterial marker detected in a sample, and generates a composite score from the individual bacterial marker scores. The scoring method is included within the scope of the present invention. In order to develop a scoring method for various bacterial markers, cut-off values for bacterial marker levels are determined. When a diagnostic method is performed, the cut-off values are used to classify the samples into different categories with respect to the levels of a bacterial marker in each category (for example, low, medium or high). In order to determine the cut-off values, levels of a bacterial marker are determined by appropriate analytical procedures in the samples obtained from a patient population. The statistical distribution of the levels of the marker in a given sample set is calculated or otherwise evaluated, quantitatively or qualitatively. For example, a fraction of the samples associated with a particular range of the levels of the marker is calculated. Based on the evaluation, cut-off values are determined. The scores to be assigned to each of the ranges are also determined. Samples are then assigned, categorized or classified into a category based the amount or levels of the marker detected in the samples. Based on the categorization, concentrations for each of the markers utilized in a particular embodiment of the test are converted into a score characteristic of the concentration or levels of the marker. The individual scores are combined into a composite score, which is used in clinical interpretation of the test results. FIG. 1 provides a schematic illustration on the distribution of several markers in a particular patient population as well as determination of the cut-off values for each marker. The scoring method according to the present invention can be flexibly adjusted to reflect distribution of various bacterial markers in various patient populations so as to achieve improved probative value and clinically meaningful diagnostic data for different sample sets, patient populations and bacterial markers.

BV diagnostic methods described herein are accurate, cost-effective, clinically predictive and readily interpretable. They are compatible with other tests for urogenital conditions and/or sexually transmitted diseases (STIs), such as candidiasis, trichomoniasis, chlamydia, gonorrhea and others. The BV diagnostic methods of the present invention are at least as sensitive and specific as the conventional tests currently employed for BV diagnosis, such as Nugent Gram stain scoring approach and Amsel interpretation, when the conventional tests are performed by skilled practitioners. They are least as sensitive but significantly more specific than tests using single molecular markers, such as BD Affirm Assay.

The BV diagnostic methods described herein utilize a relatively simple and robust design and scoring method that enables accurate differentiation of BV positive and negative samples to be performed in a standardized and cost-effective manner. BV diagnostic methods and sample scoring methods described herein provide improved clinical testing and management options for the common and problematic syndrome of bacterial vaginosis.

EXAMPLES

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated. Some of the procedures are described below for illustrative purpose.

Example 1

Clinical Evaluation

Evaluation of 396 patients was conducted with the goal of developing a clinically validated test for BV based on nucleic acid amplification, such as qPCR, and quantification of key indicator organisms. The evaluated patient population consisted of adult females at least 18 years of age. Multiple vaginal swabs were collected from each evaluated patient and tested according to standard BV diagnosis procedures (termed "gold standard"), namely, Nugent Gram-stain scoring system and Amsel criteria. Additional, vaginal swabs were tested by the Affirm test and qPCR assays for several bacterial markers. The information from different qPCR assays was used to determine BV status of each sample, and the results were statistically analyzed and compared with the results of Nugent Gram-stain scoring system, Amsel criteria and Affirm test.

Example 2

Patient Population

A total of 402 women presenting for clinical evaluation at either the Sexually Transmitted Diseases Clinic, Jefferson County Department of Public Health (JCDH), Birmingham, Ala. (299 patients), or the Personal Health Clinic (PHC), University of Alabama-Birmingham, Birmingham, Ala. (103 patients) between April and October, 2011 were enrolled in the study. All enrolled patients were over 18 years of age, and did not receive antibiotics or use vaginal medications, including antifungal medications, for at least 14 days prior to enrollment. Evaluations could not be completed on 6 enrollees, thus, the results from 396 patients were available for the clinical evaluation described in the earlier example.

Example 3

Sample Collection

Informed consent was obtained from all the patients. A series of vaginal samples was collected from each patient in order to conduct comprehensive evaluation for markers of vaginitis, including bacterial markers, *Candida* spp. and *Trichomonas vaginalis*, and testing for *Chlamydia trachomatis* and *Neisseria gonorrhoeae*. The sample series contained the samples described below. A standard vaginal swab was collected and used to prepare a smear for Gram staining procedure on a microscopy slide. The microscope slide was stained according to Gram staining procedure and assessed in the field by a qualified clinician according to the Nugent scoring system. The same vaginal swab that was used for Gram staining, was then placed in Affirm™ VPIII transport system (Becton-Dickinson, Sparks, Md.) with dropper vial additive. The second vaginal swab was collected and placed into ESwab™ (Copan Diagnostics Inc., Murrieta, Calif.) transport system for culture and confirmatory Gram stain evaluation. Two additional swabs were collected using the APTIMA™ vaginal swab collection device (GenProbe™ Inc., San Diego, Calif.) for nucleic-acid amplification testing.

Example 4

Sample Assessment According to Conventional Gold Standard Methods

For each evaluated patient, BV status was ascertained by clinical assessment using the gold standard: the Amsel criteria assessment of a vaginal secretion sample and Nugent scoring performed on a Gram-stained a vaginal swab sample.

For Amsel criteria assessment, vaginal secretions were collected from each patient and evaluated at the point of collection according to the Amsel criteria. The following standard Amsel criteria were assessed and recorded for each patient: presence of thin, whitish, homogenous vaginal discharge; amine (fishy) odor on the addition of KOH to the wet mounted vaginal discharge material, the presence of clue cells upon microscopic examination of vaginal discharge samples; and a pH value of greater than 4.5 for the vagina discharge.

Vaginal samples were also evaluated according to Nugent Gram-stain scoring system. Quantitative Gram-staining for each sample was performed according to standard procedures. In brief, a standard vaginal swab was rolled across a glass microscope slide, air dried, and then fixed in methanol prior to Gram staining. Gram-staining was performed. Gram-stained slides were then examined for specific bacterial morphologies, and Nugent scores (NS: range 0-10) generated. An NS of 0-3 was interpreted as normal or negative for BV, a score of 7-10 was interpreted as abnormal or positive for BV, and a score of 4-6 was interpreted as intermediate for BV.

In order to definitively classify samples as positive or negative for BV, the samples with intermediate NS that met the Amsel criteria for BV were classified as BV positive, and the samples with intermediate NS that failed to meet the Amsel criteria for BV were classified as BV negative.

Example 5

Sample Characterization Results Based on the Gold Standard BV Diagnostic Methods In the first phase of the study, 169 samples ("first sample group") were characterized according to the conventional gold standard methods, namely, Amsel criteria assessment and Nugent Gram-stain scoring. Of the 169 samples comprising the first sample group, 108 (63.9%) were determined to be BV positive and 61 (36.1%) were determined to be negative for BV according to the gold standard. Of the BV positive samples, 96 (88.1%) had NS of 7-10, with 12 samples having NS of 4-6 and positive Amsel results. Of the BV negative samples, 47 (77.0%) had NS of 0-3, with the remaining 14 samples being Amsel negative and NS intermediate. 168/169 (99.4%) of samples in this phase of the study were collected from patients attending the JCDH clinic. An additional 227 samples were subsequently collected ("second sample group"). One hundred and thirty one (57.7%) of these samples were obtained from patients attending JCDH, and 96 (42.3%) from patients attending PHC. Among the second sample group, 110 (48.5%) were positive and 107 (51.5%) negative for BV. Unambiguous NS were obtained for 200/227 (88.1%) of the second group samples, and of the 27 samples with intermediate NS, 8 were resolved as positive and 19 as negative using Amsel criteria. The overall prevalence of BV in the study population was, therefore, 55.1% (218/396) with an NS intermediate rate of 13.6% (54/396). Of the 54 NS intermediate samples, 21 (38.9%) resolved as positive for BV using the Amsel criteria.

Example 6

Nucleic Acid Isolation

Nucleic-acid was extracted from vaginal swab suspensions prepared and stored in APTIMA™ collection system using the MagNAPure LC™ Total Nucleic Acid Isolation Kit on MagNAPure™ LC Instruments (Roche Applied Science, Indianapolis, Ind.) according to the manufacturer's instructions. Prior to extraction, DNA Sample Processing Reagent (DNA-SPR; EraGen Biosciences, Madison, Wis.; 5 µl) was added to each specimen. DNA-SPR contains a proprietary, extractable, DNA target that is used as an internal control in PCR assays to monitor recovery of nucleic-acid and elimination of PCR inhibitors through sample preparation. Nucleic acid was eluted in a final volume of 50 μl and either analyzed immediately or stored at a temperature of less than −20° C.

Example 7

Quantitative PCR Assays

For quantitative PCR (qPCR) testing of the samples for the presence of *A. vaginae*, BVAB-2, *Megasphaera*-1, *G. vaginalis* and *L. crispatus*, primer designs were developed for each of the organisms based on in silico analysis of published 16S rRNA gene sequences and are shown in Table 1. The primers were screened for multiplex qPCR compatibility and lack of cross-reactivity. Assays were designed for use the primer-based MultiCode®-RTx system (EraGen Biosciences, Madison, Wis.) for real-time product detection. Generally, the MultiCode®-RTx system exploits the physico-chemical properties of two unique synthetic nucleotide bases and allows for specific amplification of PCR products to be monitored as concentration-dependent decreases in fluorescence, with confirmation of amplification of the desired product accomplished post-amplification via determination of peak melting temperatures ($T_m$) of amplified products.

One member of each primer pair used in the qPCR assay for multiple markers contained a 2'-deoxy-5-methyl-isocytidine (iC) base coupled to a fluorescein moiety immediately proximal to the 5'-terminus of the molecule. For quantitative measurement of the respective analytes, synthetic oligonucleotide Ultramers™ (Integrated DNA Technologies Inc., Coralville, Iowa) were used to construct calibrating material. Each Ultramer contained the target sequence of one of the intended analytes, and quantitative analytical data provided by the manufacturer was used as the basis for value assignment (in DNA copies) of these materials. All qPCR assay runs included a set of 3 ultrameric calibrators, and interpolation of crossing threshold ($C_t$) values generated during PCR amplification of vaginal samples into calibration curves enabled the derivation of DNA concentrations per mL of sample for each analyte. A total of 5 μL of extracted nucleic-acid (corresponding to 20 μL of original vaginal sample), was utilized for qPCR amplification reactions, and the dynamic range of all qPCR assays was established at $1 \times 10^3$-$1 \times 10^8$ copies/mL. Amplification reactions were performed on RotorGene™ Q instruments (QiaGen Inc., Chatsworth, Calif.) using the following conditions: initial denaturation for 2 min at 95° C., 50 cycles of amplification (95° C.×5 sec, 58° C.×10 sec, 72° C.×20 sec (fluorescence collected during this step); with post-amplification melt analysis (60° C. to 95° C. ramp, 1.0° C. per second).

Example 8

Multiplexed qPCR Assay

The BV PCR design consisted of a pair of multiplexed PCR reactions. BV-1 contained the *A. vaginae* primer pair (5-carboxyfluorescein (FAM) labeled) and an internal control primer pair (6-hexachlorofluorescein (HEX) labeled). BV-2 contained the BVAB-2 primer pair (FAM labeled) and the *Megasphaera*-1 primer-pair (HEX labeled). Each BV PCR run contained 2 ultrameric calibrators for the Av reaction (set at 7.0 $\log_{10}$ copies/mL for Cal-1 and 5.5 $\log_{10}$ copies/mL for Cal-2), 2 ultrameric calibrators for the BVAB-2 reaction (set at 6.0 $\log_{10}$ copies/mL for Cal-1 and 4.5 $\log_{10}$ copies/mL for Cal-2), and a single ultrameric calibrator for *Megasphaera*-1 set at 6.0 $\log_{10}$ copies/mL. Each run also contained appropriate negative and positive extraction controls to monitor assay performance.

Example 9 qPCR Testing Results Using Single Known BV Bacterial Markers

Five organisms were separately detected by qPCR in the 169 samples of the first sample group: *A. vaginae*, BVAB-2, *G. vaginalis*, *Megasphaera*-1 and *L. crispatus*. Comparison of qPCR testing results obtained for each separate marker and gold standard results is illustrated in Table 2. All four of the qPCR-detected organisms that are known to be positive BV markers were frequently present in samples designated as BV positive. Using an assay cut-off value of $1 \times 10^3$ copies/mL, 98.1% (106/108) BV positive samples were positive for *G. vaginalis*, 98.2% (106/108) of the BV positive samples were positive for *A. vaginae*, 89.8% (97/108) of the BV positive samples were positive for BVAB-2, and 87.0% (94/108) of the BV positive samples were positive for *Megasphaera*-1.

The frequency with which these organisms were found in BV negative samples were appreciably different among the organisms. 60.7% (37/61) of BV negative samples were positive for *G. vaginalis*, 52.5% (32/61) positive for *A. vaginae*, 18.0% (11/61) for BVAB-2, and 16.4% (10/61) for *Megasphaera*-1.

TABLE 1

Primer sequences used to detect indicated 16s rRNA regions of target organisms

| Target | Primer ID | Sequence (5' → 3') | 5'-Location | GenBank Accession Number |
|---|---|---|---|---|
| *A. vaginae* | AvFP-BV1 | FAM-isodC-CCC TGG TAG TCC TAG CT$^a$ (SEQ ID NO: 1) | 746 | AJ585206 |
|  | AvRP-BV1 | CGG CAC GGA AAG TAT AAT CT (SEQ ID NO: 2) | 808 | |
| BVAB-2 | BvabFP-BV2 | FAM-isodC-CGT GTA GGC GGC TAG ATA AGT G (SEQ ID NO: 3) | 199 | GQ900639 |
|  | BvabFP-BV2 | TCC AGC ACT CAA GCT AAA CAG TTT GT (SEQ ID NO: 4) | 283 | |
| *G. vaginalis* | Gv-16s-F1 | FAM-isodC-GTG ACA TGG TGC TAA TCC CT (SEQ ID NO: 5) | 1226 | HQ114564 |
|  | Gv-16s-F2 | GCT GCC CAC TTT CAT GAC TT (SEQ ID NO: 6) | 1388 | |

TABLE 1-continued

Primer sequences used to detect indicated 16s rRNA regions of target organisms

| Target | Primer ID | Sequence (5' → 3') | 5'-Location | GenBank Accession Number |
|---|---|---|---|---|
| Megasphaera-1 | MegaFP-BV2 | GCT CTG TTA TAC GGG ACG AAA AAG (SEQ ID NO: 7) | 419 | AB279971 |
|  | MegaRP-BV2 | FAM-isodC-CGG ACG GAT ACT GTT GGC ATC (SEQ ID NO: 8) | 462 |  |
| L. crispatus | Lc-16s-F1 | CAG GTC TTG ACA TCT AGT GCC (SEQ ID NO: 9) | 969 | HQ716720 |
|  | Lc-16s-F2 | ATT TFAM-isodC-CAT GCA CCA CCT GTC TTA G (SEQ ID NO: 10) | 1041 |  |

[a]FAM: 5-carboxyfluorescein is used as the reporter dye and is coupled to the initial 5'-nucleotide in the primer.
isodC: 2'-deoxy-5-methyl-isocytidine is the initial nucleotide at the 5'-end of the fluorescently labeled primer.

Analysis of the distribution of quantitative values also demonstrated appreciable differences in organism concentrations in BV positive and negative sample populations, as illustrated in Table 2. The median concentration observed in BV positive and negative populations differed by 3.5 $\log^{10}$ copies/mL for *G. vaginalis*, 3.8 $\log^{10}$ copies/mL for *A. vaginae*, >3.1 $\log^{10}$ copies/mL for BVAB-2, and >3.9 $\log^{10}$ copies/mL for *Megasphaera*-1.

*L. crispatus* was evaluated as a negative BV marker and was found at an unexpectedly low rate in the study population with only 37/169 (21.9%) samples having >1×103 copies/mL of this organism. The frequency of detection of *L. crispatus* in BV positive samples was significantly lower than that observed in BV negative samples (10.2% v 42.6%; p<0.01), however, a majority (57.4%) of BV negative samples in this population lacked detectable levels of this organism.

Analysis of data generated from the single marker qPCR tests demonstrated that the utility of *A. vaginae* and *G. vaginalis*, highly sensitive markers for BV, was limited by their low specificity, or high frequency with which they were identified in samples from patients not classified as BV positive. BVAB-2 and *Megasphaera*-1 were somewhat more specific indicators of BV positivity than either *G. vaginalis* or *A. vaginae*, but at least one of these organisms was present in a significant subset of BV negative study subjects.

Example 10

Statistical Analysis of qPCR Data for Known Marker Organisms

Statistical analysis of qPCR data obtained for known marker organisms indicated that no single marker organism reliably differentiated between BV positive and BV negative samples. *G. vaginalis* and *A. vaginae* each demonstrated high sensitivity, but limited concentration discrimination observed for each of these organisms between the $4^{th}$ quartile of the negative population and the $1^{st}$ quartile of the positive sample population compromised specificity. BVAB-2 and *Megasphaera*-1, by contrast, demonstrated lower overall sensitivity, but greater concentration discrimination between positive and negative populations.

Logistic regression analysis (MedCalc Software Suite) was performed on all marker combinations using the results obtained for the 169 samples of the first sample group (illustrated in Table 3). BV status of the patients, based on NS plus Amsel criteria was used as the dependent variable (negative=0, positive=1), and the qPCR results of the combinations of marker organisms were used as the independent variable. The results of this analysis demonstrated that certain combinations of three marker organisms, namely, *A. vaginae*/BVAB-2/*Megasphaera*-1 or *G. vaginalis*/BVAB-2/*Megasphaera*-1, offered advantageous combination of sensitivity

TABLE 2

Results of quantitative PCR measurements of marker organisms in vaginal samples identified as positive or negative for BV according to gold standard.

| Organism | BV Status[a] | PCR Results[b] | | qPCR Values ($\log_{10}$ copies/mL) | | |
|---|---|---|---|---|---|---|
|  |  | Negative | Positive | $25^{th}$ Pct | $50^{th}$ Pct | $75^{th}$ Pct |
| A. vaginae | Negative | 29 | 32 | <3.00 | 3.11 | 4.98 |
|  | Positive | 2 | 106 | 6.52 | 6.90 | 7.32 |
| BVAB-2 | Negative | 50 | 11 | <3.00 | <3.00 | <3.00 |
|  | Positive | 11 | 97 | 5.38 | 6.04 | 6.64 |
| G. vaginalis | Negative | 24 | 37 | <3.00 | 3.48 | 5.31 |
|  | Positive | 2 | 106 | 6.61 | 6.99 | 7.53 |
| Megasphaera-1 | Negative | 51 | 10 | <3.00 | <3.00 | <3.00 |
|  | Positive | 14 | 94 | 6.18 | 6.89 | 7.18 |
| L. crispatus | Negative | 35 | 26 | <3.00 | <3.00 | 7.55 |
|  | Positive | 97 | 11 | <3.00 | <3.00 | <3.00 |

[a]BV status was defined based on a combination of Nugent Gram-stain score (NS) and Amsel's criteria. BV positive samples were those with NS value of 7-10 and samples with NS values of 4-6 that met Amsel's criteria.
[b]Samples that generating qPCR values below the lower limit of quantitation of the respective assays (1000 copies/mL) were considered negative. Pct is an abbreviation for "percentile."

and specificity, with both parameters exceeding 90% for these combinations (illustrated in Table 3).

None of the tested combination of two markers reported in this example generated both sensitivity and specificity parameters of >90% in the development phase sample cohort. This finding unexpectedly contradicts the earlier reports by others on a reasonable specificity for BV using a qualitative combination of *A. vaginae* and *G. vaginalis*, or that qualitative detection of either BVAB-2 or *Megasphaera*-1 was highly sensitive and specific when compared against either NS or Amsel criteria.

The experimental data summarized in this example indicated that a combination of BVAB-2 and *Megasphaera*-1 also lacked a high level of specificity, even if only samples with NS values of ≤7 are considered as positive and intermediate NS samples excluded from analysis. Of the 47 samples in the first sample group with NS of ≤3, 9 (19.1%) had positive results for either BVAB-2 (2 samples), *Megasphaera*-1 (4 samples), or both organisms (3 samples), using a threshold for positivity of $1\times10^3$ copies/mL. Performance of this combination using only the Amsel criteria for BV designation was even less probative, with either *Megasphaera*-1 or BVAB-2 DNA detected in 26/72 (36.1%) Amsel negative samples in the first sample group. These results were unexpected in view of the earlier studies by others using comparable value assessment (the median quantitative values for each of the markers in BV positive patients in the earlier studies were only 0.5 $\log_{10}$ DNA copies per sample higher than those described here).

analysis of the first sample group described in this example unexpectedly demonstrated that quantitative analysis of these 2 markers, in combination, was not able to reliably differentiate BV positive from BV negative samples.

Example 11

Three-Marker Test Performance Using Individual qPCR Detection for Each Marker Organism A test employing qPCR testing of three bacterial marker organisms ("three-marker qPCR test") was developed. In this example, individual qPCR analysis of vaginal samples for each organism was employed to detect the concentrations of each of *A. vaginae*, BVAB-2 and *Megasphaera*-1 bacteria.

Analytical cut-off values were selected to categorize the samples, as illustrated by FIG. 1. Frequency distributions of the values generated by qPCR for the three selected marker organisms (*A. vaginae*, BVAB-2, and *Megasphaera*-1) were compared against designation of samples by NS. Breakpoint values were selected that best differentiated sample populations into 'high' 'medium' and 'low' categories, correlating with 'high', 'intermediate' and 'low' NS. For *Megasphaera*-1 (see FIG. 1, panel C), an intermediate category was not created because of the sharp breakpoint associated with the transition from low to high qPCR values.

The individual marker organisms were scored according to the criteria set forth in Table 4. The total (or composite) test score was calculated as the sum of the individual scores, as

TABLE 3

Results of logistic regression analysis of qPCR results for various marker organism combinations

| Number of Markers | Organisms[a] | BV Status[b] | PCR Category[b] | | Statistical Metrics | |
|---|---|---|---|---|---|---|
| | | | Negative | Positive | Sensitivity | Specificity |
| 2 | Av/BVAB-2 | Negative | 50 | 11 | 95.4% | 82.0% |
| | | Positive | 5 | 103 | | |
| | Av/Gv | Negative | 47 | 14 | 95.4% | 77.0% |
| | | Positive | 5 | 103 | | |
| | Av/Mega-1 | Negative | 53 | 8 | 94.4% | 86.9% |
| | | Positive | 6 | 102 | | |
| | BVAB-2/Gv | Negative | 50 | 11 | 96.3% | 82.0% |
| | | Positive | 4 | 104 | | |
| | BVAB-2/Mega-1 | Negative | 54 | 7 | 92.7% | 88.5% |
| | | Positive | 7 | 101 | | |
| | Gv/Mega-1 | Positive | 53 | 8 | 93.5% | 86.9% |
| | | Negative | 7 | 101 | | |
| 3 | Av/BVAB-2/Gv | Negative | 51 | 10 | 95.4% | 83.6% |
| | | Positive | 5 | 103 | | |
| | Av/BVAB-2/Mega-1 | Negative | 55 | 6 | 95.4% | 90.2% |
| | | Positive | 5 | 103 | | |
| | Av/Gv/Mega-1 | Negative | 53 | 8 | 94.4% | 86.9% |
| | | Positive | 6 | 102 | | |
| | BVAB-2/Gv/Mega-1 | Negative | 55 | 6 | 93.5% | 90.0% |
| | | Positive | 7 | 101 | | |
| 4 | Av/BVAB-2/Gv/Mega-1 | Negative | 52 | 9 | 95.4% | 85.2% |
| | | Positive | 5 | 103 | | |

[a]Av = *Atopobium vaginae*, Gv = *Gardnerella vaginalis*, Mega-1 = *Megasphaera*-1.
[b]BV status was defined based on a combination of Nugent Gram-stain score (NS) and Amsel criteria. BV positive samples were those with NS value of 7-10 and samples with NS values of 4-6 that met Amsel criteria.
[c]Categorized using logistic regression analysis, with BV status as the dependent variable (negative = 0; positive = 1), and qPCR results on the 169 samples of the first sample group for the different marker combinations as the independent variable.

Figure 2:
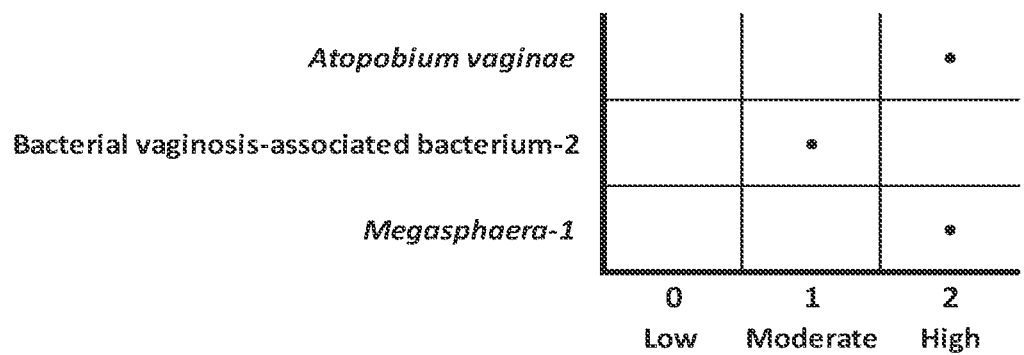
FIG. 2 is a scheme illustrating interpretation of the results of the quantitative testing using composite score based on the individual scores for *A. vaginae*, BVAB-2 and *Megasphaera*-1.

Yet another earlier report by others stated that a combination of *A. vaginae* and *G. vaginalis* analyzed quantitatively may be used to accurately differentiate BV positive from negative samples, using threshold concentrations of $10^8$ copies/mL and $10^9$ copies/mL, respectively. Logistic regression illustrated in FIG. 2. The sum of each organism's score equals the total score. As discussed earlier, samples with a total score of 0-1 were considered negative for BV, samples with a score of 3-6 were considered positive for BV, and samples with a score of 2 were considered indeterminate for BV. The total score interpretation is schematically illustrated in Table 5. The composite scores were compared to the previously determined BV designations of the samples, as illustrated in Table 6. The interpretive assignment of results and their comparison with the gold-standard results obtained for the same sample group is shown in Table 7. The composite score demonstrated good correlation with the BV designation by NS and Amsel for a majority of the samples. Composite cores of 3-6 were highly correlated with positive samples, with 96.1% (98/102) of samples yielding these scores being BV positive. Similarly, a score of 0 was highly correlated with negative samples, with 93.9% (46/49) of samples yielding this score being BV negative.

The remaining 18 samples (10.7%; 11 BV negative, 7 BV positive) yielded composite scores of 1-2. Of the 10 samples with a composite score of 1; 2 had NS of ≤3, 6 had NS scores of 4-6, and 2 had NS of ≥7. Of the 8 samples with a composite score of 2; 2 had NS of ≤3, 3 had NS scores of 4-6, and 2 had NS of ≥7. The samples with composite scores of 2 were designated as 'indeterminate' for the purpose of BV diagnosis. It was determined that since the composite score of 2 required the presence of any of the 3 marker organisms at high concentration, or at least 2 of them (*A. vaginae* and BVAB-1) at moderate concentrations, this score is indicative of deviation from normal vaginal flora, however, only a subset of the samples could be classified as BV using conventional test methods. Samples generating a composite score of 1 were designated as BV-negative. Upon excluding samples generating a score of 2 from the final analysis, the predicted sensitivity and specificity of the BV PCR construct on the remaining 161 samples were 93.3% (98/105) and 92.9% (52/56), respectively, with an indeterminate rate of 4.7% (8/169).

The experimental results reported in this example demonstrated that inclusion of markers with high degree of specificity, for example BVAB-2 and *Megasphaera*-1, as well as markers with a high degree of sensitivity, is advantageous in order to produce a qPCR test for BV having improved positive predictive value or values. Three-marker tests using qPCR assay for *A. vaginae*, BVAB-2, and *Megasphaera*-1 provided an advantageous combination of sensitivity and specificity, achieving 93.5% correlation (158/169) with the combined NS and Amsel gold standard.

Example 12 qPCR Sample Characterization and Scoring

Upon completion of a qPCR assay, results were exported into an MS Excel worksheet for scoring according to the scheme shown in Table 4. Composite scores (sum of 3 individual analyte scores) were then compiled, and the final interpretation generated as follows: BV Negative (scores of 0-1), BV Indeterminate (score of 2), BV Positive (scores of 3-6), as illustrated in Table 5.

TABLE 4

Scoring system used to categorize the samples analyzed by qPCR assay

| Organism | Organism Concentration ($\log_{10}$ DNA copies/mL) | | |
| --- | --- | --- | --- |
| *Atopobium vaginae* | ≤5.5 | 5.5-7.0 | >7.0 |
| BVAB-2 | ≤4.5 | 4.5-6.0 | >6.0 |
| Megasphaera-1 | ≤6.0 | n/a | >6.0 |
| Score | Low = Score of 0 | Moderate = Score of 1 | High = Score of 2 |

TABLE 5

Total score interpretation

Total
Score Interpretation 3-6 Positive - indicative of bacterial vaginosis
0-1 Negative - not indicative of bacterial vaginosis
2 Indeterminate - unable to determine BV status. Additional clinical laboratory data should be evaluated to establish a diagnosis.

Certain characteristics of qPCR testing (qPCR assay in combination with scoring and score interpretation) were determined as follows:

positive predictive value (PPV)=sensitivity/(sensitivity+(1−prevalence)(1−specificity))negative predictive value (NPV)=

((1−prevalence)specificity)/((1−prevalence)+prevalence((1−sensitivity))sensitivity=samples determined as positive by qPCR testing/samples determined as positive by the gold standard specificity=samples negative by qPCR testing/samples negative by the gold standard Example 13

Three-Marker Test Performance Using Multiplexed qPCR Assay Detection

Performance of the three marker qPCR test was tested using a multiplexed qPCR assay to analyze samples for the presence of the three bacterial markers: *A. vaginae*, BVAB-2 and *Megasphaera*-1 bacteria. Incorporation of nucleic-acid calibrators in each qPCR run, at the concentrations determined by qPCR analysis to be most probative in differentiating populations of samples, allowed for categorization of samples without the need for fully quantitative PCR analysis. The samples of the first sample-group were analyzed with the three-marker test using multiplexed PCR, and the results of this BV diagnostic determination are shown in Table 6. The interpretive assignment of results and their comparison with the gold-standard results obtained for the same sample group is shown in Table 7. These results were highly congruent with those obtained by using individual qPCR assays for each marker with only 5 of 169 samples (2.9%) generating categorically different results. These changes resulted in one additional BV positive sample being classified as positive by BV PCR, one additional BV negative sample being classified as negative by BV PCR, two BV negative samples moving from an indeterminate to a negative PCR score, and one BV positive sample moving from a positive to an indeterminate PCR score. Overall, therefore, 162/169 (95.9%) of the samples generated interpretable composite PCR scores in the multiplexed qPCR three-marker test, with the sensitivity of the assay being 94.2% (98/104) and the specificity 94.8% (55/58).

The additional 227 samples belonging to the second sample group were also evaluated by the multiplexed qPCR three-marker test. A substantial minority of the samples of the second sample group were collected at the lower BV prevalence PHC location, thus the overall prevalence of BV in the second sample group was 48.5% as compared to the 64.5% BV prevalence in the first sample group. The score assignments for the combined first and second sample groups generated by multiplexed qPCR three-marker test (396 samples) are shown in Table 6, and the interpretive results and comparison to the gold-standard results for the second sample group and the combined sample group is shown in Table 7.

Results obtained for the second sample group were generally comparable to those obtained on the first sample group, thus supporting the validity of the scoring system created based on the individual qPCR testing. Of the 227 samples in the second sample group, 14 (6.2%) yielded a composite score of 2 and were thus deemed indeterminate for BV, of which 9 were BV negative samples and 5 BV positive samples. In the total population tested, 21 samples generated a BV PCR score of 2, 9 (42.9%) of these were BV positive samples and 12 (57.1%) were BV negative samples, supporting the use of 'indeterminate' as a categorical designation for specimens generating this composite PCR score. Of the 213 samples that generated an evaluable PCR score in the second sample group, 104 of 105 (99.0%) BV positive samples generated a positive PCR score, and 98 of 108 (90.7%) BV negative samples generated a negative score. Of the 17 samples in the second sample group that generated a composite PCR score of 1, only 1 was a BV positive sample, confirming the appropriateness of categorizing samples with this score as BV negative.

Analysis of the combined sample group (396 samples) demonstrated that the three-marker qPCR test using multiplexed qPCR had a sensitivity of 96.7% (202/209), a specificity of 92.2% (153/166), a positive predictive value of 94.0% and a negative predictive value of 95.6%, with an indeterminate rate of 5.3% (21/396).

Using a combination of three marker organisms, *A. vaginae*, BVAB-2, and *Megasphaera*-1, in an assay format that segregated samples into marker-specific populations (high, medium, low) based on their relationship to breakpoint DNA concentrations, enabled 94.7% (375/396) of the samples of the combined sample group to be categorized with respect to the presence or absence of BV with an overall accuracy of 94.7% (355/396). Analysis of the 20 samples generating discordant results between BV status determined by qPCR test and BV status by NS and Amsel criteria revealed the challenge of attempting to correlate molecular data for this condition with conventional techniques.

Analysis of the samples generating discordant results between the three-marker qPCR test and BV status by NS and Amsel criteria revealed that the three-marker qPCR test detected patient-specific changes in microflora that may not be detected by conventional clinical methods. Of the 13 BV negative samples that were positive by BV PCR, only 3 had NS of ≤3, and of the 7 BV positive samples that were negative by BV PCR only 1 had an NS of ≥7, and this patient was negative by Amsel criteria. Thus only 4/20 (20%) of the results discordant between the three marker qPCR test determination and gold-standard test determination could be unambiguously categorized by NS, the remainder were NS intermediate samples, a cohort likely to have significant, patient-specific, variation in the extent of correlation of symptoms with specific changes in microflora.

TABLE 6

Distribution of composite PCR scores by BV status

| Sample Set | Assay[a] | BV Status | Composite PCR Score | | | | | | |
|---|---|---|---|---|---|---|---|---|---|
| | | | 0 | 1 | 2 | 3 | 4 | 5 | 6 |
| First Sample Group (n = 169) individual | qPCR | Negative (61) | 46 | 6 | 5 | 1 | 3 | 0 | 0 |
| | | Positive (108) | 3 | 4 | 3 | 11 | 29 | 32 | 26 |

TABLE 6-continued

Distribution of composite PCR scores by BV status

| Sample Set | Assay[a] | BV Status | Composite PCR Score | | | | | | |
|---|---|---|---|---|---|---|---|---|---|
| | | | 0 | 1 | 2 | 3 | 4 | 5 | 6 |
| qPCR assay | BV-PCR | Negative (61) | 46 | 9 | 3 | 2 | 1 | 0 | 0 |
| | | Positive (108) | 3 | 3 | 4 | 17 | 25 | 29 | 27 |
| First Sample Group (n = 169) multiplexed qPCR assay) | BV-PCR | Negative (117) | 82 | 16 | 9 | 3 | 6 | 1 | 0 |
| | | Positive (110) | 0 | 1 | 5 | 8 | 29 | 25 | 42 |
| Combined Sample Group (n = 396) | BV-PCR | Negative (178) | 128 | 25 | 12 | 5 | 7 | 1 | 0 |
| | | Positive (218) | 3 | 4 | 9 | 25 | 54 | 54 | 69 |

[a]qPCR: Individual quantitative determinations of analyte concentrations. Scores determined by comparison of qPCR values with breakpoint concentrations established from frequency distributions of development phase sample cohort; BV-PCR: Semi-quantitative assay using internal calibrators to assign individual analyte scores.

TABLE 7

Correlation of interpretive results generated from BV PCR assay analysis of samples with gold-standard results.

| Sample Set | BV Status | BV PCR Result | | |
|---|---|---|---|---|
| | | Positive | Negative | Indeterminate |
| First Sample Group (n = 169) | BV Positive | 98 | 6 | 4 |
| | BV Negative | 3 | 55 | 3 |
| Second Sample Group (n = 227) | BV Positive | 104 | 1 | 5 |
| | BV Negative | 10 | 98 | 9 |
| Combined Sample Group (n = 396) | BV Positive | 202 | 7 | 9 |
| | BV Negative | 13 | 153 | 12 |

Example 14

Bacterial Marker Selection for the BV Diagnostic Test

A combination of three BV-positive marker organisms (*Atopobium vaginae*, BVAB-2, and *Megasphaera*-1) resulted in a three-marker qPCR test producing BV diagnostic results in agreement with the conventional gold standard techniques for diagnosing BV. It was determined that inclusion of at least one positive marker organisms with high sensitivity but lower specificity and one positive marker organism with lower sensitivity but higher specificity resulted in unexpectedly advantageous performance characteristics of a multi-marker test, such as predictive value.

Relative quantitation of large Gram-positive rods, a morphotype consistent with a number of peroxide-producing *Lactobacillus* spp. (such as, *L. crispatus, L. iners, L. jensenii*), organisms was previously reported as important for maintaining a healthy vaginal environment and therefore constitutes a significant component (40%) of the total NS. Utility of *G. vaginalis* and *L. crispatus* for improving the positive predictive value of a multi-marker qPCR test was therefore assessed. PCR assays for *G. vaginalis* and *L. crispatus* was performed, as discussed in the earlier examples. The quantity of *G. vaginalis*, as measured by the qPCR assay, was found to be less predictive of BV than the three markers included in the three-marker qPCR test.

*L. crispatus* was evaluated, as discussed in an earlier example, since this organism was previously described as commonly present in low NS samples across diverse patient populations. In the first sample group, *L. crispatus* DNA was detected in 42.6% of BV negative samples and only in 10.2% of BV positive samples, and median quantitative values of *L. crispatus* in samples containing this organism were significantly higher in the BV negative population ($8.9 \times 10^7$ copies/mL versus $4.1 \times 10^4$ copies/mL; p<0.01), consistent with earlier reports that the presence of this organism is inversely associated with the presence of BV. Examination of the results for other marker organisms in *L. crispatus*-positive samples, however, unexpectedly revealed that in only a single instance was *L. crispatus* detected in a BV negative sample that was scored as positive based on the combination of *A. vaginae*, BVAB-2, and *Megasphaera*-1 qPCR results.

In addition, high *L. crispatus* DNA levels were strongly correlated with the absence of significant concentrations of positive predictive marker organisms. No samples in the first sample set containing an *L. crispatus* concentration of $>5.1 \times 10^5$ copies/mL (n=23) generated a composite BV PCR score in the BV-positive range. Unexpectedly, it was found the inclusion of *Lactobacillus* organism in the final assay design would not, therefore, have improved the accuracy of positive results. The data reported herein showed that molecular determination of BV can be achieved using positive predictive markers, thus resulting in a simpler multi-marker test. It was previously documented that the significance of hydrogen peroxide-producing *Lactobacillus* species to the overall vaginal microflora of healthy women differs considerably based on ethnic background. Depending on the ethnic background of the patient and/or other factors, variations of multi-marker tests may include or exclude negative predictive markers, such as *L. crispatus*.

Example 15

Flexible Adjustments of the Multi-Marker qPCR Test and Assessment of the Performance Characteristics A three-marker multiplexed qPCR test described herein allowed a semi-quantitative assessment of the DNA concentrations of key positive predictive markers, maintaining the probative advantage of classifying samples by concentration afforded by qPCR, but doing so in a simplified and highly reproducible assay format. The classification boundaries described herein were based on the frequency distribution data for BV markers in a sample set, as illustrated in shown in FIG. 1. Classification of vaginal populations based on assignment of a numerical score directly related to critical concentrations of marker organisms unexpectedly resulted in a multi-marker test having improved performance characteristics, such as predictive value. However, these classification boundaries can be changed or adjusted for a particular sample set based on the statistical data in order to achieve improvements in performance characteristics in a particular population.

One advantage of the multi-marker tests described herein is that, since they generates results on a discrete numerical scale, the performance characteristics of the test in any given population can be estimated by comparing the frequency distribution of composite scores in that population with the accuracy of each score derived from the data presented here. Based on the analysis of the experimental data summarized in the examples presented herein, in which a score of 0 had a negative predictive value of 97.6% (125/128), whilst a score of 5 or 6 had a positive predictive value of 99.2% (123/124), it can be understood that the proportion of samples in a population generating these three values strongly influences the overall predictive value of the a multi-marker qPCR test described herein.

The frequency distribution of composite scores generated by samples submitted for the assay during the first two months after its introduction into routine testing were examined, and this examination demonstrated that in this unselected clinical population with a prevalence of BV (as determined by BV PCR) of 26.3%, and an indeterminate rate of 6.2%, 81.2% of samples tested generated scores of 0, 5, or 6, resulting in estimated positive and negative predictive values of 95.1% and 96.8%, respectively. An ability to assess performance characteristics of the multi-marker qPCR test in a given population allows for advantageously improved clinically meaningful interpretation of the test results, as compared to previously known BV tests. Also, the performance characteristics of the multi-marker qPCR test can be compared to other tests, this allowing the clinicians to select the most advantageous test for a particular situation.

Data generated based on the combined sample set and summarized in Table 8 indicated a sensitivity and specificity for Affirm™ test of 89.9% and 71.1%, and for the three-marker qPCR test of 96.7% and 92.2%, respectively. Based on these data, predictive values were calculated for Affirm™ and three-marker qPCR test for hypothetical populations with different BV prevalence. The results are shown in Table 9.

TABLE 8

Affirm ™ test performance evaluated with respect to the gold-standard BV determination

| Affirm ™ test results | Gold standard results | | Affirm ™ test performance | |
| --- | --- | --- | --- | --- |
| | Negative | Positive | | |
| Negative | 173 | 123 | 50 | 71.10% specificity |
| Positive | 218 | 22 | 196 | 89.91% sensitivity |

TABLE 9

Calculated predictive value of Affirm and three-marker qPCR tests based on BV prevalence in a hypothetical patient population.

| Test | BV prevalence in a hypothetical patient population | Calculated predictive value | |
| --- | --- | --- | --- |
| Affirm | 40% | 67.4% PPV | 91.4% NPV |
| | 30% | 57.1% PPV | 94.3% NPV |
| | 20% | 43.4% PPV | 96.3% NPV |
| | 10% | 25.4% PPV | 98.3% NPV |
| Three-marker qPCR | 40% | 89.2% PPV | 97.7% NPV |
| | 30% | 84.1% PPV | 98.4% NPV |
| | 20% | 75.7% PPV | 99.1% NPV |
| | 10% | 58.1% PPV | 99.6% NPV |

Depending on the BV prevalence in a hypothetical patient population within the range shown in Table 9 (10%-40%), the advantageous increase in PPV for the three-marker q-PCR test as compared to the Affirm™ test, ranges between approximately 22-33%.

Different arrangements and combinations of the elements and the features described herein are possible. Similarly, some features and subcombinations are useful and may be employed without reference to other features and subcombinations. Embodiments of the invention and examples have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the invention.

What is claimed is:

1. A kit for assessing bacterial vaginosis (BV) status in a female, comprising primers containing a fluorescent reporter dye coupled to synthetic initial 5'-nucleotide and other reagents for detecting in a sample obtained from the female nucleic acid sequences characteristic of positive marker BV-associated bacteria wherein the bacteria are BVAB-2, *Megasphaera*-1 and at least one of *Atopobium vaginae* or *Gardnerella vaginalis* and wherein the kit does not contain reagents for detecting a *Lactobacillus bacterium*.

2. The kit of claim 1, wherein the fluorescent reporter dye comprises a fluorescein moiety.

3. The kit of claim 1, wherein the primers contain a 2'-deoxy-5-methyl-isocytidine base coupled to a fluorescein moiety immediately proximal to 5' terminus.

4. The kit of claim 1, wherein the positive marker BV-associated bacteria are BVAB-2, *Megasphaera*-1 and *Atopobium vaginae* or *Gardncrclla vaginalis*.

5. The kit of claim 1, wherein the kit comprises pairs of primers for conducting a quantitative PCR assay or a semi-quantitative PCR assay for detecting BVAB-2, *Megasphaera*-1 and at least one of *Atopobium vaginae* or *Gardnerella vaginalis*.

6. The kit of claim 1, wherein the positive marker BV-associated bacteria are BVAB-2, *Megasphaera*-1 and *Gardnerella vaginalis*.

7. The kit of claim 1, wherein the kit comprises at least three pairs of primers for conducting a quantitative PCR assay or a semi-quantitative PCR assay for detecting BVAB-2, *Megasphaera*-1 and *Atopobium vaginae*, and does not contain pairs of primers for detecting a *Lactobacillus bacterium*.

8. A kit for assessing bacterial vaginosis (BV) status in a female, comprising pairs of primers containing a fluorescent reporter dye coupled to synthetic initial 5'-nucleotide for detecting in a sample obtained from the female by a multiplexed quantitative or a semi-quantitative PCR assay nucleic acid sequences characteristic of BVAB-2, *Megasphaera*-1 and at least one of *Gardnerella vaginalis* or *Atopobium vaginae*, wherein the kit does not contain reagents for detecting a *Lactobacillus bacterium*.

9. The kit of claim 8, comprising pairs of primers characteristic of BVAB-2, *Megasphaera*-1 and *Gardnerella vaginalis*.

10. The kit of claim 8, comprising pairs of primers characteristic of BVAB-2, *Megasphaera*-1 and *Atopobium vaginae*.

11. The kit of claim 8, wherein the pairs of primers are selected from the group consisting of pairs of primers for detecting BVAB-2, *Megasphaera*-1 and *Atopobium vaginae*.

\* \* \* \* \*

SEQUENCE LISTING

<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is 2'-deoxy-5-methyl-isocytidine

<400> SEQUENCE: 1
nccctggtag tcctagct                                              18

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
cggcacggaa agtataatct                                            20

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is 2'-deoxy-5-methyl-isocytidine

<400> SEQUENCE: 3
ncgtgtaggc ggctagataa gtg                                        23

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4
tccagcactc aagctaaaca gtttgt                                     26

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is 2'-deoxy-5-methyl-isocytidine

<400> SEQUENCE: 5
ngtgacatgg tgctaatccc t                                          21

<210> SEQ ID NO 6
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 6
gctgcccact ttcatgactt                                               20

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
gctctgttat acgggacgaa aaag                                          24

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is 2'-deoxy-5-methyl-isocytidine

<400> SEQUENCE: 8
ncggacggat actgttggca tc                                            22

<210> SEQ ID NO 9
<211> LENGTH: 25
<212> TYPE: DNA
<213> ORGANISM: Artificial Sequence
<220> FEATURE:
<223> OTHER INFORMATION: Synthetic Construct

<400> SEQUENCE: 9
caggtcttga catctagtgc cattt                                         25

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is 2'-deoxy-5-methyl-isocytidine

<400> SEQUENCE: 10
ncatgcacca cctgtcttag                                               20
```